US008641750B2

(12) United States Patent
Bicek et al.

(10) Patent No.: US 8,641,750 B2
(45) Date of Patent: Feb. 4, 2014

(54) STENT DESIGN WITH SHEATH ATTACHMENT MEMBERS

(75) Inventors: Andrew D. Bicek, Big Lake, MN (US); Timothy S. Girton, Maple Grove, MN (US)

(73) Assignee: LifeShield Sciences LLC, Plano, TX (US)

( * ) Notice: Subject to any disclaimer, the term of this patent is extended or adjusted under 35 U.S.C. 154(b) by 993 days.

(21) Appl. No.: 11/857,531

(22) Filed: Sep. 19, 2007

(65) Prior Publication Data

US 2008/0009935 A1 Jan. 10, 2008

Related U.S. Application Data

(62) Division of application No. 09/974,653, filed on Oct. 10, 2001, now Pat. No. 7,399,312.

(51) Int. Cl.
*A61F 2/06* (2013.01)

(52) U.S. Cl.
USPC ........................................... 623/1.12

(58) Field of Classification Search
USPC ........... 623/1.12, 1.13, 1.44, 1.46, 1.36, 1.11; 606/108, 192, 194
See application file for complete search history.

(56) References Cited

U.S. PATENT DOCUMENTS

| 5,411,550 | A | 5/1995 | Herweck et al. |
| 5,618,299 | A | 4/1997 | Khosravi et al. |
| 5,628,788 | A | 5/1997 | Pinchuk |
| 5,681,345 | A * | 10/1997 | Euteneuer ................. 623/1.11 |
| 5,693,085 | A | 12/1997 | Buirge et al. |
| 5,733,328 | A | 3/1998 | Fordenbacher |
| 5,749,880 | A | 5/1998 | Banas et al. |
| 5,824,046 | A | 10/1998 | Smith et al. |
| 5,865,723 | A | 2/1999 | Love |
| 5,911,754 | A * | 6/1999 | Kanesaka et al. ............ 623/1.15 |
| 5,916,264 | A | 6/1999 | Von Oepen et al. |
| 5,989,244 | A | 11/1999 | Gregory et al. |
| 5,990,379 | A | 11/1999 | Gregory |
| 6,087,552 | A | 7/2000 | Gregory |
| 6,110,212 | A | 8/2000 | Gregory |
| 6,206,888 | B1 | 3/2001 | Bicek et al. |
| 6,224,626 | B1 | 5/2001 | Steinke |
| 6,231,598 | B1 * | 5/2001 | Berry et al. .................. 623/1.15 |
| 6,296,661 | B1 | 10/2001 | Davila et al. |
| 6,506,408 | B1 | 1/2003 | Palasis |
| 6,575,994 | B1 | 6/2003 | Marin et al. |
| 6,767,359 | B2 * | 7/2004 | Weadock .................... 623/1.14 |
| 7,462,190 | B2 * | 12/2008 | Lombardi .................... 623/1.13 |

FOREIGN PATENT DOCUMENTS

| EP | 0 960 607 A1 | 12/1999 |
| WO | WO 00/12147 | 3/2000 |
| WO | WO 01/66035 | 9/2001 |

* cited by examiner

*Primary Examiner* — Victor Nguyen
(74) *Attorney, Agent, or Firm* — Vidas, Arrett & Steinkraus, P.A.

(57) ABSTRACT

A stent is provided having attachment members for allowing attachment of a sheath or sheaths. Accordingly, a practitioner is able to selectively choose a desirable sheath, such as a polymeric sleeve, a biomaterial, or a natural blood vessel, at a point-of-use and attach it to the sheath. The attachment members may be bendable tabs and/or secondary support stents.

26 Claims, 2 Drawing Sheets

STENT DESIGN WITH SHEATH ATTACHMENT MEMBERS

CROSS-REFERENCE TO RELATED APPLICATIONS:

This is a divisional application of application Ser. No. 09/974,653, filed Oct. 10, 2001, now U.S. Pat. No. 7,399,312, the entire content of which is incorporated by reference herein.

BACKGROUND OF THE INVENTION

1. Field of the Invention

This invention relates to vascular stents and, more particularly, to covered vascular stents.

2. Description of Related Technology

In the prior art, it is known to provide a covering for an implantable vascular stent, such as that disclosed in U.S. Pat. No. 5,916,264. Such covered stents or stent/grafts are used for a variety of vascular treatments, but have particular usefulness in endovascular applications to support or maintain the patency of the natural vessel. Depending on the particular needs of a patient, a specific stent/cover combination is chosen as a treatment. Generally, however, stent coverings are emplaced on the stent at a manufacturing facility. As a result, medical practitioners have been traditionally limited in their selection of a stent and covering combination to what is commercially available.

To overcome some of the deficiencies of the prior art, mountable sheaths for emplacement onto a stent have been developed which allow a practitioner to select a particular sheath and stent combination at a point-of-use, beyond the manufacturing facility. A mountable sheath is disclosed in WIPO International Publication No. WO 00/12147, the applicant of which is the same as the assignee herein. The mountable sheath is slitted to facilitate mounting onto a stent, and may be treated with a pharmaceutical agent, radioactive agent, bioactive agent, or a combination thereof. The sheath is attached and retained on the stent using compressive force, glue, a protective sheath, or socks. The compressive force is generated radially (inwardly and/or outwardly), by the sheath itself, the stent, or both. It is, however, desired to provide a simplified method of attaching and retaining the mountable sheath, as well as other sheaths, to a stent.

SUMMARY OF THE INVENTION

The present invention provides a means for selecting and joining a particular stent configuration and a particular covering or lining for the stent to tailor the final stent/graft device to a particular patient.

With the subject invention, a stent is provided having a radially-expandable body with axial ends, wherein at least one bendable tab extends from one of the ends. The tab is formed to be bendable so as to at least partially overlap the body upon being bent. Accordingly, a sheath or cover can be concentrically arranged (internally and/or externally) of the stent, with the tab being bent into engagement with the sheath so as to provide a holding force therein.

In one aspect of the invention, a tubular stent is provided with a plurality of circumferentially spaced tabs extending from each end. The construction of the stent may be of any configuration or material known in the art.

It is preferred that the tabs be unitarily formed from or integral with the stent, such as by being laser-cut from the same stock in forming the stent. In one embodiment of the invention, the tab is connected to the stent via a single stem which allows for relative easy bending thereof. To ensure low-risk of failure (i.e., tab separation from the stent), the stem may be strengthened by forming it thicker than the stent, using known metal-working processes, or by the application of a strengthening agent, such as a coating, cladding, and the like. Alternatively, the stem may be formed thinner than the stent to enhance bendability of the tab. Furthermore, the tab is preferably formed with a non-linear shape (such as with a U-shape, V-shape, circle shape, box shape, triangular shape, rectangle shape, and so forth) so as to provide a distributed area of contact force (as opposed to point contact or line contact) upon the sheath, with the arms of the tab diverging to further enhance this effect. To ensure that the tabs maintain their bent sheath-engagement positions during use, the tabs are preferably formed from a deformable material with little recoil or elasticity, such as stainless steel, tantalum, niobium, or a platinum-enhanced alloy.

The sheath may be formed from a polymer sleeve such as a PTFE, ePTFE, polyurethane, polypropylene, polyester or other biocompatible material. In another aspect of the invention, the polymer sleeve may be formed of a biodegradable material. Bioactive or therapeutic agents, such as drugs or biological materials may be incorporated in or on the polymeric sleeve for release subsequent to implantation. The sleeve may also be formed from a biomaterial such as elastin or collagen, or from a section of natural blood vessel (e.g., saphenous vein). With the subject invention, a physician, or other practitioner, can selectively choose the type of sheath required, as well as the type of pre-implantation treatment thereof. For example, a physician may choose to soak a polymeric sleeve in a particular therapeutic agent prior to implantation.

Once selected, the sheath may be fixed externally or internally of the stent, by disposing it concentrically therewith, and bending the tabs accordingly to engage and secure the sheath to the stent. As an alternative embodiment, multiple sheaths can be disposed internally or externally of the stent, with the tabs holding the composite structure in place. Furthermore, one or more sheaths can be simultaneously disposed internally and externally of the stent, with a portion of the tabs being bent inwardly to provide holding force for the internal sheath(s) while a portion of the tabs are bent externally to provide a holding force for the external sheath(s).

A tool may be provided for bending the tabs in assisting a practitioner.

As a second embodiment of the subject invention, one or more secondary support stents may be utilized to hold the sheath or sheaths relative to the stent. In one variation, a ring-shaped support stent, having a much shorter axial length than the main stent, may be plastically deformed (e.g. by crimping) in proximity to an end of the main stent to provide necessary holding force for the sheath(s). One or more of such support stents may be used internally and/or externally of the main stent, as required.

These and other features of the invention will be better understood through a study of the following detailed description and accompanying drawings.

DETAILED DESCRIPTION OF THE INVENTION

Figure 1:
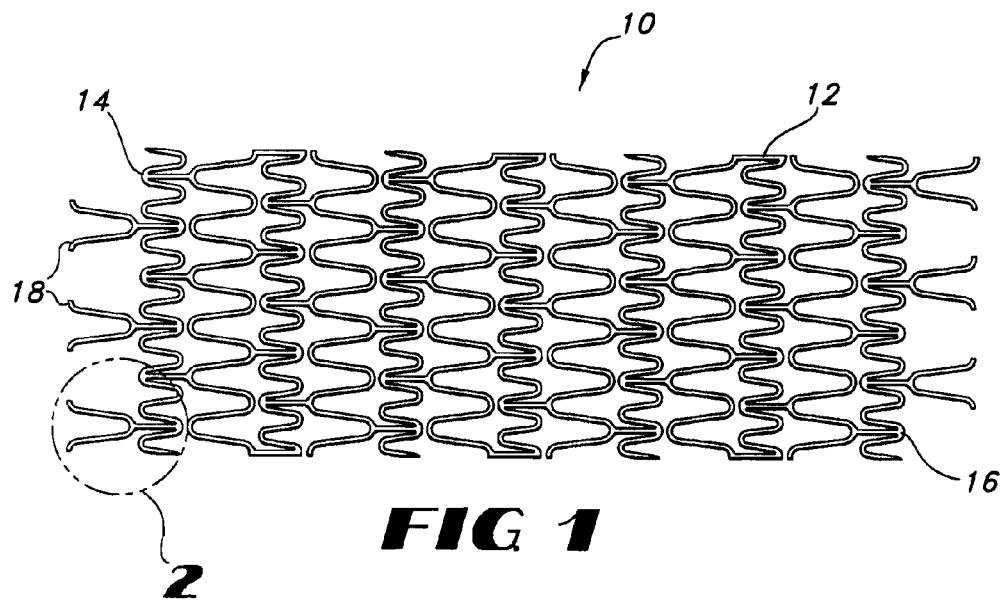
FIG. 1 is a side elevational view of a stent having bendable tabs formed in accordance with the subject invention.

With the subject invention, a device and method are provided for allowing practitioners to selectively choose a sheath as a covering for a stent at a point-of-use. With this versatility, a practitioner has the ability to utilize not only polymeric sheaths, but also biomaterial and natural material, and allow for such to be treated prior to implantation, such as soaking in a therapeutic agent. The subject invention may be used in the coronary vasculature, esophagus, trachea, colon, biliary tract, urinary tract, prostate and brain.

With reference to FIGS. 1-4, a first embodiment of the subject invention is depicted, wherein a stent 10 is provided having a tubular body 12, a first axial end 14, and a second axial end 16. One or more bendable tabs 18 extend from the first and/or second axial ends 14, 16.

The stent 10 may be of any stent configuration known to those skilled in the art, including those used alone or in a stent-graft arrangement. Various stent types and stent constructions may be employed in the present invention including, without limitation, self-expanding stents and balloon expandable stents. The stents may be capable of radially contracting as well. Self-expanding stents include those that have a spring-like action which cause the stent to radially expand or stents which expand due to the memory properties of the stent material for a particular configuration at a certain temperature. Other materials are of course contemplated, such as stainless steel, platinum, gold, titanium, tantalum, niobium, and other biocompatible materials, as well as polymeric stents. The configuration of the stent may also be chosen from a host of geometries. For example, wire stents can be fastened in a continuous helical pattern, with or without wave-like forms or zigzags in the wire, to form a radially deformable stent. Individual rings or circular members can be linked together such as by struts, sutures, or interlacing or locking of the rings to form a tubular stent.

It is preferred that the stent 10 be of the type that is etched or cut (e.g., laser cut) from a unitary cylindrical stock. Accordingly, the tabs 18 desirably may be cut from the same stock as the tubular body 12 and be formed unitarily therewith. Desirably, the tubular body 12 is radially-expandable using conventional techniques, such as balloon distension, or may be self-expanding.

Figure 2:
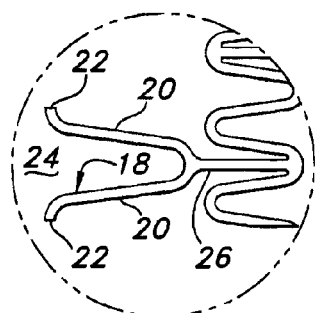
FIG. 2 is an enlarged view of section 2 of FIG. 1.

With reference to FIG. 2, in one embodiment, the tabs 18 have a generally U-shape with side legs 20 which slightly diverge. With this structural configuration, the tabs 18 may distribute holding force over an area, rather than have point contact or line contact (e.g., if a single slender wire was to be used). The side legs 20 terminate in free ends 22 which are flared slightly outwardly from an open mouth 24 of the tab. It is desired to ensure that sharp edges are eliminated from the tabs 18, especially at the free ends 22 to prevent unintended puncture of the vessel. Because the tabs 18 may be located externally of an implanted stent, and in contact with a vein wall, it is desired to ensure that micromovement of the tabs will not result in any abrading damage to the vein wall. Advantageously, where the tabs 18 may be unitarily laser cut with the tubular body 12, electropolishing of the entire assembly removes all sharp edges.

It is preferred that the tabs 18 have a shape which imparts a holding force over an area, such as a v-shape, circle shape, box shape, triangular shape, rectangular shape and so forth with the tab 18 being defined by an element outlining the shape, or being at least partially solid across the area of the tab (e.g., a solid disc). It is preferred to use a configuration other than a slender linear shape so that, as mentioned above, holding force is distributed over an area. A flattened or deformed wire may also distribute a holding force over an area.

The tab 18 is connected to the body 12 via a stem 26 which is bendable. With unitary manufacturing of the tabs 18 and the body 12, the stem 26 will have the same thickness as other parts of the stent 10. It may be desired, however, to strengthen the stem 26 so as to reduce the likelihood of failure thereof which may result in separation of the tabs 18 from the body 12. The stem 26 may be strengthened in a variety of ways, such as: by providing additional material therein to thicken it; using known metal-working techniques; and/or providing a strengthening agent, such as a coating, cladding, or the like. The stem 26 is formed of sufficient length to allow the tab 18 to be bent thereabout to at least partially overlap the body 12. Alternatively, it may be desired to form the stem 26 thinner than surrounding portions to enhance the bendability thereof. Also, the stem 26 may be thinned to increase its cross-sectional width so as to provide a holding force over a larger area.

Figure 3:
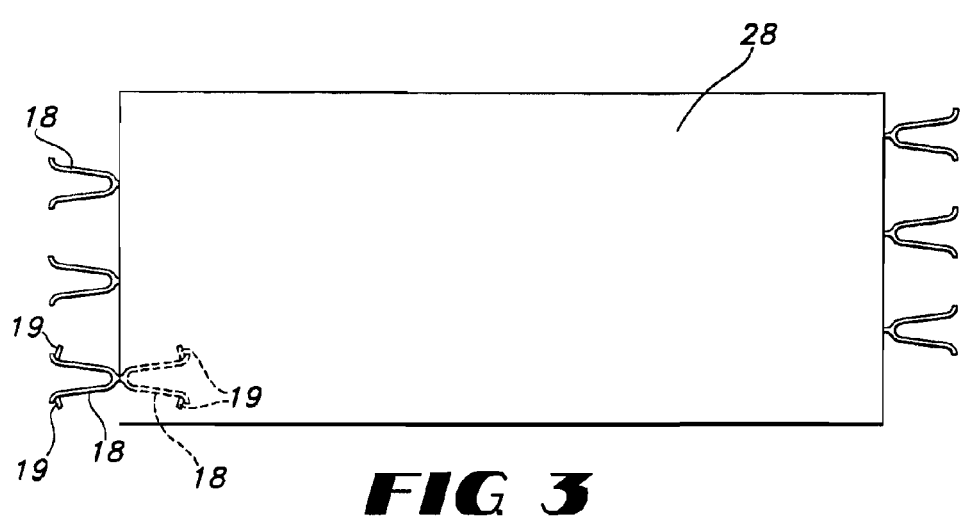
FIG. 3 is an elevational view of the subject invention having a sheath disposed about the body of the stent.

With reference to FIG. 3, the stent 10 is covered by a sheath 28 with the tabs 18 extending from the assembly. As previously discussed, the sheath 28 may be formed from any number of materials, including synthetic or natural polymers, biomaterials, or natural materials, such as natural blood vessel (e.g., a saphenous vein). The sheath 28 may have a tubular shape, or be slitted as shown in WIPO International Publication No. WO 00/12147. The entire disclosure of WIPO International Publication No. WO 00/12147 is incorporated herein by reference herein.

As shown in FIG. 3, the sheath is concentrically disposed relative to the stent 10 (as shown in FIG. 3 disposed, for example, radially outwardly) and one or more of the tabs 18 are caused to be bent into engagement therewith. Accordingly, the sheath 18 is attached to the stent 10 and shall be retained relative thereto by the holding force of the tabs 18. It is desired to have the tabs 18 sufficiently bent so that the tabs 18 are recessed within, or flush with, the sheath 28. Accordingly, it is desirable that no portion of the tabs 18 shall extend outwardly from the assembly.

To ensure that the tabs 18 maintain their bent positions after application, the tabs 18 are preferably formed from a deformable material with little recoil or elasticity, such as stainless steel, tantalum, niobium, or a platinum-enhanced alloy. Shape memory alloys, such as nitinol, can be used so long as the tabs 18 are treated to not re-gain their original unbent shape once implanted.

Figure 4:
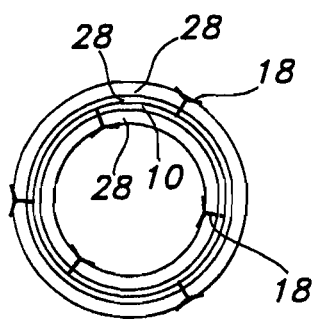
FIG. 4 is an end elevational view of the subject invention having multiple sheaths; and, FIG. 5 is an elevational view of a second embodiment of the subject invention using crimped support stents.

With reference to FIG. 4, multiple sheaths 28 may be disposed externally of the stent 10. Likewise, one or more of the sheaths 28 may be disposed radially inwardly of the stent 10, with one or more of the tabs 18 being bent inwardly into engagement with the sheath(s) 28. As a further variation, one or more sheaths 28 may be simultaneously disposed internally and externally of the stent 10, with a portion of the tabs 18 being bent inwardly, and a portion of the tabs 18 being bent outwardly.

Because of the ability to apply the sheath 28 at the point-of-use, a practitioner may choose to treat the sheath 28 prior to implantation, such as soaking with one or more of the following therapeutic agents: anti-thrombogenic agents (such as heparin, heparin derivatives, urokinase, and PPack (dextrophenylalanine proline arginine chloromethylketone); anti-proliferative agents (such as enoxaprin, angiopeptin, or monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); antineoplastic/antiproliferative/anti-miotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl keton, an RGD peptide-containing compound, heparin, antithrombin compounds, platelet receptor antagonists, anti-thrombin antibodies, anti-platelet receptor antibodies, aspirin, prostaglandin inhibitors, platelet inhibitors and tick antiplatelet peptides); vascular cell growth promotors (such as growth factor inhibitors, growth factor receptor antagonists, transcriptional activators, and translational promotors); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vascoactive mechanisms. In addition, radioactive agents and bioactive agents may be used in various combinations, along with the therapeutic agents listed above.

Figure 5:
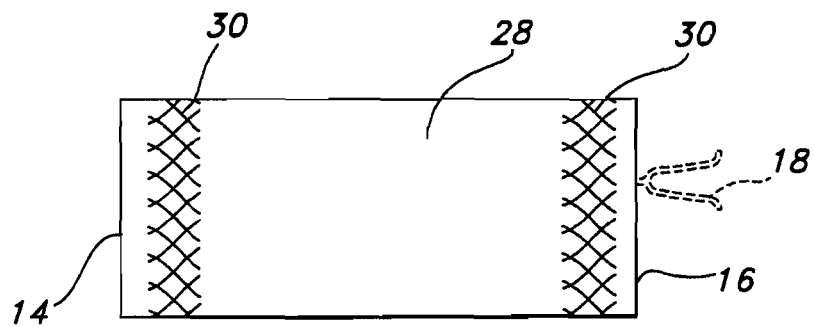

The stent 10 may take any form, such as a "box car" type stent, which utilizes discrete stent elements linked together by flexible connections, such as that shown in FIG. 5 of U.S. Pat. No. 5,693,085. The entire disclosure of U.S. Pat. No. 5,693,085 is incorporated by reference herein. With a "box car" stent, the tabs 18 will only extend from the end elements, and not the central stent elements. It is also possible to form the stent 10 with tabs extending only from one axial end 14, 16 of a tubular stent, and only one of the tabs 18 at the respective axial end 14, 16 may be required depending on the application (e.g., amount of holding force required). It is preferred to use a plurality of the tabs 18 with such tabs 18 being circumferentially evenly-spaced, such as with three tabs 18 at each axial end 14, 16 located at intervals of 120 degrees relative to the circumference of the body 12. In this manner, an even distribution of holding force can be achieved to ensure proper fixing of the sheath 28 to the stent 10.

Conventional techniques may be used to implant the stent 10/sheath 28 assembly. As a further variation, one or more barbs 19 may be formed on one or more of the tabs 18 which are formed to puncture a surrounding vessel wall upon implantation of the assembly. The barbs 19 need only be formed on the side of the tabs 18 which will be externally exposed with a completed assembly, and preferably, are formed in proximity to the free ends 22. The barbs 19 shall act to provide additional holding force for the structure at a desired location.

A hand tool (not shown) may also be provided to aid a practitioner in bending the tabs 18.

In a second embodiment of the invention, one or more ring-shaped support stents 30 replace the tabs 18 to provide holding force for the sheath 28. With reference to FIG. 5, the support stents 30 generate a relative pressing force with the stent 10 (hidden from view) to hold the sheath 28 in place. As with the tabs 18, if shape memory alloys are used in forming the support stents 30, it is desired to treat the support stents 30 such that will prevent the support stents 30 from re-gaining their original shape. It is also desirable that no portion of the stent 10 come into contact with the support stents 30.

In one variation, the support stents 30 may be plastically-deformed to provide, and maintain, the necessary holding force. For example, the support stents 30 may be crimped. The support stents 30 may be partially plastically deformed, such at discrete points or along a region, or may be wholly plastically deformed. Any plastic deformation of the support stents 30 should not interfere with the ability of the stent 10 and the sheath 28 to be implanted (i.e., interfere with the ability to radially compress and radially expand). Alternatively, the support stents 30 and/or the stent 10 may generate a radial pressing force which holds the sheath 28.

It is preferred that the support stents 30 be of limited axial length and not be coextensive with the body 12 of the stent 10. To avoid end separation of the sheath 28 from the stent 10, the support stents 30 are disposed in proximity to the axial ends 14, 16. It is possible to use only one of the support stents 30, such as at the upstream axial end 14, 16 of the stent 10 relative to blood flow. In addition, as shown in dashed lines, it is possible to form at least one tab 18 at one axial end 14, 16 in connection with the use of one or more of the support stents 30 to supplement the holding force thereof. As an alternative, a single support stent 30 may be used which extends over a major extent of the sheath 28.

The support stents 30 may be of any construction known in the art. The structure may be plastically-deformable upon being crimped radially inwardly or outwardly.

As with the first embodiment, multiple sheaths 28 may be disposed internally and/or externally, with the support stents 30 providing holding force intraluminally. If there is reliance on plastic deformation of the support stents 30, the support stents 30 may be crimped radially outwardly to hold any internally-disposed sheaths 28.

To facilitate the plastic deformation of the support stents 30, a tool (not shown) may be provided.

Various changes and modifications can be made to the present invention. It is intended that all such changes and modifications come within the scope of the invention as set forth in the following claims.

What is claimed is:

1. A stent comprising a radially-expandable body having first and second axial ends, and at least one bendable tab extending from said first axial end, each bendable tab comprising two free ends, each bendable tab having a first configuration and a second configuration, when the bendable tab is in the first configuration the two free ends of the bendable tab are directed in a first direction and when the bendable tab is in the second configuration the two free ends are directed in a second direction opposite the first direction, the bendable tab at least partially overlapping the body in the second configuration;
wherein said at least one tab is connected to said body via a single bendable stem, the stem being straight when the bendable tab is in the first configuration, the stem having a bend when the bendable tab is in the second configuration.

2. The stent as in claim 1, wherein said stent is generally cylindrical.

3. The stent as in claim 1, wherein at least one bendable tab extends from said second axial end, said tab being bendable to at least partially overlap said body.

4. The stent as in claim 1, wherein a plurality of said tabs extend from said first axial end.

5. The stent as in claim 1, wherein said at least one tab has a non-linear shape.

6. The stent as in claim 1, wherein said at least one tab is unitarily formed with said body.

7. The stent as in claim 1, further comprising at least one barb extending from at least one said tab.

8. The stent as in claim 1, wherein said at least one tab has a U or V shape with side legs terminating in the free ends forming an open mouth therebetween.

9. The stent as in claim 8, wherein said side legs of said tab diverge.

10. The stent as in claim 8, wherein said free ends of said side legs are flared outwardly.

11. The stent as in claim 1, wherein said stem is strengthened to reduce likelihood of failure upon bending.

12. The stent as in claim 1, wherein said stem is provided with a strengthening agent, wherein the strengthening agent is either a coating or a cladding.

13. The stent as in claim 1, wherein said stem has a thinner profile than surrounding portions of the stent to facilitate enhanced bending.

14. The stent as in claim 1, wherein the stent at said axial end has a ring of wave or zig-zag form, said stem being integral with said ring at a valley of said wave or zig-zag form and extending until beyond the peaks of said wave of zig-zag form.

15. The stent as in claim 1, wherein one or more barbs are formed in said tab.

16. The stent of claim 1, further comprising a first sheath, the sheath being between the at least one bendable tab and the stent when the tab is in the second configuration.

17. A stent comprising a radially-expandable body having first and second axial ends, and at least one bendable tab extending from said first axial end, each bendable tab comprising two free ends, each bendable tab having a first configuration and a second configuration, when the bendable tab is in the first configuration the two free ends of the bendable tab are directed in a first direction and when the bendable tab is in the second configuration the two free ends are directed in a second direction opposite the first direction, the bendable tab at least partially overlapping the body in the second configuration
wherein said tab generates a relative pressing force with said body to hold a sheath in place, said sheath being not bonded to said tab with said pressing force solely acting to hold said sheath in place.

18. A prosthesis comprising:
a plurality of circumferential bands, one of the plurality of circumferential bands forming a first end of the prosthesis, another of the plurality of circumferential bands forming a second end of the prosthesis,
the plurality of circumferential bands including first circumferential bands of a first wavelength, each first circumferential band comprising:
a plurality of first struts interconnected by a plurality of first turns directed towards a first end of the prosthesis and a plurality of second turns directed towards a second end of the prosthesis, each turn engaged to two of the plurality of first struts forming a first unit of the first circumferential band, the first unit having a first configuration;
a plurality of tabs, each tab comprising a turn and two second struts, a first end of each second strut engaged to the turn and a second end of each second strut being a free end, the turn and two second struts of the tab having a second configuration, the second configuration being the same as the first configuration of the first unit of the first circumferential band, each tab engaged to an end of the prosthesis;
a first sheath, the first sheath engaged to the prosthesis by at least some of the plurality of tabs.

19. The prosthesis of claim 18, the first unit having a size and the tab having a size equal to the size of the first unit.

20. The prosthesis of claim 18, the plurality of tabs comprising three first tabs and three second tabs, each first tab engaged to the first end of the prosthesis and each second tab engaged to the second end of the prosthesis.

21. The prosthesis of claim 18, each tab connected to the end of the stent by a stem, the stem being engaged to the turn of the tab.

22. The prosthesis of claim 18, the plurality of circumferential bands further comprising second circumferential bands of a second wavelength, each second circumferential band comprising:
a plurality of struts interconnected by a plurality of first turns directed towards a first end of the prosthesis and a plurality of second turns directed towards a second end of the prosthesis.

23. The prosthesis of claim 22, the first and second circumferential bands alternating from the first end of the prosthesis to the second end of the prosthesis.

24. The prosthesis of claim 23, one second circumferential band forming the first end of the prosthesis and another second circumferential band forming the second end of the prosthesis.

25. The prosthesis of claim 22, the second wavelength being less than the first wavelength.

26. The prosthesis of claim 18, wherein the first sheath is radially adjacent to the plurality of circumferential bands and the first sheath is radially adjacent to the at least some of the plurality of tabs, the first sheath being between the plurality of circumferential bands and the at least some of the plurality of tabs.

* * * * *